(12) United States Patent
Bagby

(10) Patent No.: US 11,564,696 B2
(45) Date of Patent: Jan. 31, 2023

(54) FIRST AT SCENE TRAUMA TREATMENT

(71) Applicant: First At Scene Trauma Treatment F.A.S.T.T., Ashland City, TN (US)

(72) Inventor: Caleb Johnson Bagby, Ashland City, TN (US)

(73) Assignee: FIRST AT SCENE TRAUMA TREATMENT F.A.S.T.T., Ashland City, TN (US)

( * ) Notice: Subject to any disclaimer, the term of this patent is extended or adjusted under 35 U.S.C. 154(b) by 585 days.

(21) Appl. No.: 16/716,263

(22) Filed: Dec. 16, 2019

(65) Prior Publication Data

US 2020/0187958 A1    Jun. 18, 2020

Related U.S. Application Data

(60) Provisional application No. 62/779,853, filed on Dec. 14, 2018.

(51) Int. Cl.
*A61B 17/132* (2006.01)
*A61F 13/00* (2006.01)
(Continued)

(52) U.S. Cl.
CPC ........ *A61B 17/1325* (2013.01); *A61B 17/132* (2013.01); *A61B 17/1327* (2013.01);
(Continued)

(58) Field of Classification Search
CPC .............. A61B 17/132; A61B 17/1325; A61B 17/1327; A61B 17/1322;
(Continued)

(56) References Cited

U.S. PATENT DOCUMENTS

| 6,593,508 B1 | 7/2003 | Harder |
| 7,652,190 B2 * | 1/2010 | Johnson ................ A61F 13/069 606/201 |

(Continued)

FOREIGN PATENT DOCUMENTS

| WO | WO1997029689 A1 | 8/1997 |
| WO | WO-2015048660 A1 * | 4/2015 ......... A61B 17/1322 |

OTHER PUBLICATIONS

"Mass Casualty Bleeding Prevention Kit—2 Person", https://www.liveactionsafety.com/mass-casualty-bleeding-prevention-kit-2-person/?gclid=Cj0KCQiA8f_eBRDcARIsAEKwRGck_r8vOVwR60_9G8b-LwALN2IESeM8yohoYjYouuwkdPn8s3F5wy8aAj_FEALw_wcB.

(Continued)

*Primary Examiner* — Tan-Uyen T Ho
*Assistant Examiner* — Bridget E. Rabaglia

(57) ABSTRACT

A medical bandaging and tourniquet system for use in dressing puncture wounds is provided. The medical bandaging and tourniquet system includes a primary dressing, a secondary dressing, a band, a tightening buckle, a retaining clip, and a tightening rod. The primary dressing serves as a main wrapping bandage that mounts the secondary dressing and tourniquet components together. The secondary dressing removably attaches to the primary dressing and serves as a bandage that can be installed onto minor wounds. The band connects to the primary dressing, serving as an elastic tourniquet band. The tightening buckle and the retaining clip are connected to the primary dressing. The tightening rod is positioned between the tightening buckle and the retaining clip. The primary dressing straps tightly along a wound though the tightening buckle. The strap is further compressed by turning the tightening rod. The tightening rod can then be secured to the retaining clip.

8 Claims, 7 Drawing Sheets

(51) Int. Cl.
*A61F 13/02* (2006.01)
*A61F 13/62* (2006.01)

(52) U.S. Cl.
CPC .......... *A61F 13/0233* (2013.01); *A61F 13/62* (2013.01); *A61F 2013/00106* (2013.01)

(58) Field of Classification Search
CPC . A61B 2017/12004; A61F 2013/00106; A61F 2013/00089; A61F 2013/00085; A61F 2013/00225; A61F 2013/0028
USPC .................. 606/203, 204; 602/40, 53, 75
See application file for complete search history.

(56) References Cited

U.S. PATENT DOCUMENTS

| | | |
|---|---|---|
| 7,776,064 B2 | 8/2010 | Jennifer et al. |
| 7,842,067 B2 | 11/2010 | Esposito |
| 9,855,055 B2 | 1/2018 | Kosiorek et al. |
| 2009/0062842 A1* | 3/2009 | Esposito ............ A61B 17/1327 606/203 |

OTHER PUBLICATIONS

"Israeli Emergency Bandage—4"", https://www.liveactionsafety.com/israeli-emergency-bandage-4/?gclid=Cj0KCQiA8f_eBRDcARIsAEKwRGdudLurFWJrBoT7dr4SvS8NeEPOup4NCARTbTQXGYDDmRDe20msaDcaAnqoEALw_wcB.

* cited by examiner

FIRST AT SCENE TRAUMA TREATMENT

The current application claims a priority to the U.S. provisional patent application Ser. No. 67/779,853 filed on Dec. 14, 2018. The current application is filed on Dec. 16, 2019 while Dec. 14, 2019 was on a weekend.

FIELD OF THE INVENTION

The present invention relates generally to a combinate tool, particularly a medical bandaging and tourniquet system that may disassemble into additional bandaging systems.

BACKGROUND OF THE INVENTION

Presently, the CDC (Center for Disease Control and Prevention) rates unintentional injury as one of the leading causes of death, despite trauma and first aid kits being known to the art, wherein the constituent elements of the kit are conventionally discretized and isolated. However, this can pose problems as the constituent components thereof can be exhausted prior to an emergency and neglected resupply thereof or overlooked for particular constituent elements. Further; in an emergency, if a constituent component of a trauma kit is somehow misplaced due to the spectrum of tools and sizes thereof, the kit itself will prove subpar or negligible in addressing an emergency situation such as stabilizing a wound. As such, it is the objective of the present invention to incorporate a combination of conventional trauma treatment tools.

SUMMARY OF THE INVENTION

Figure 1:
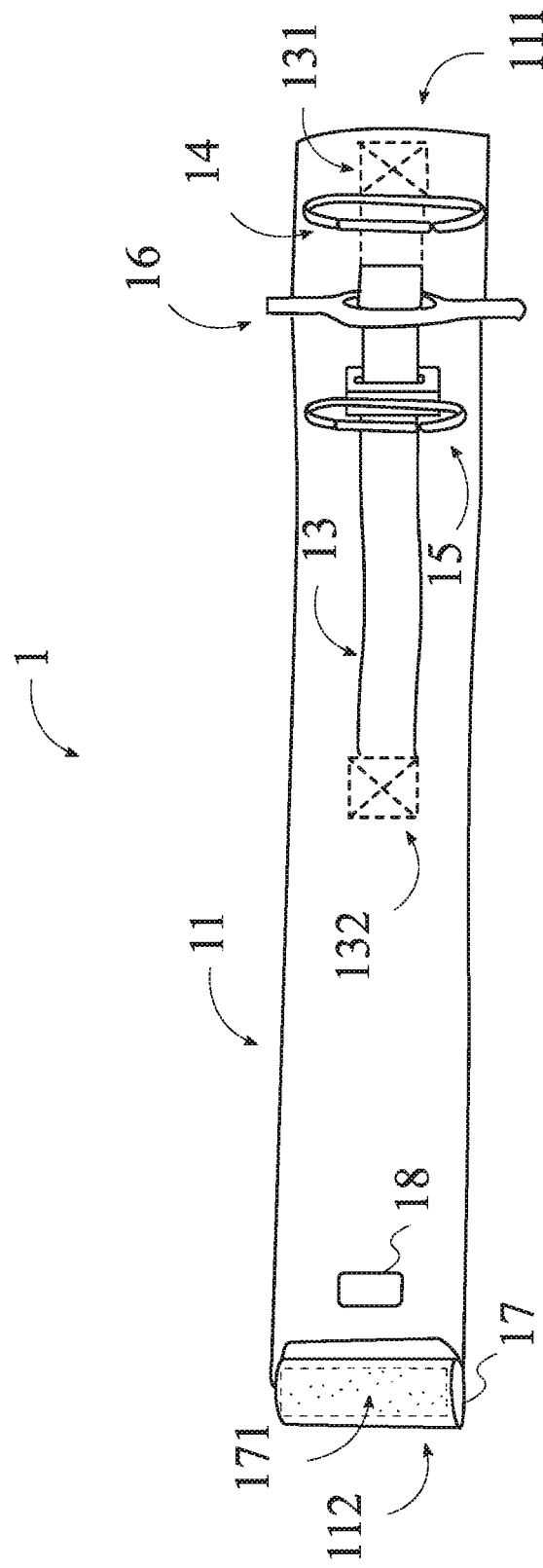
FIG. 1 is a front view of the present invention.
Figure 2:
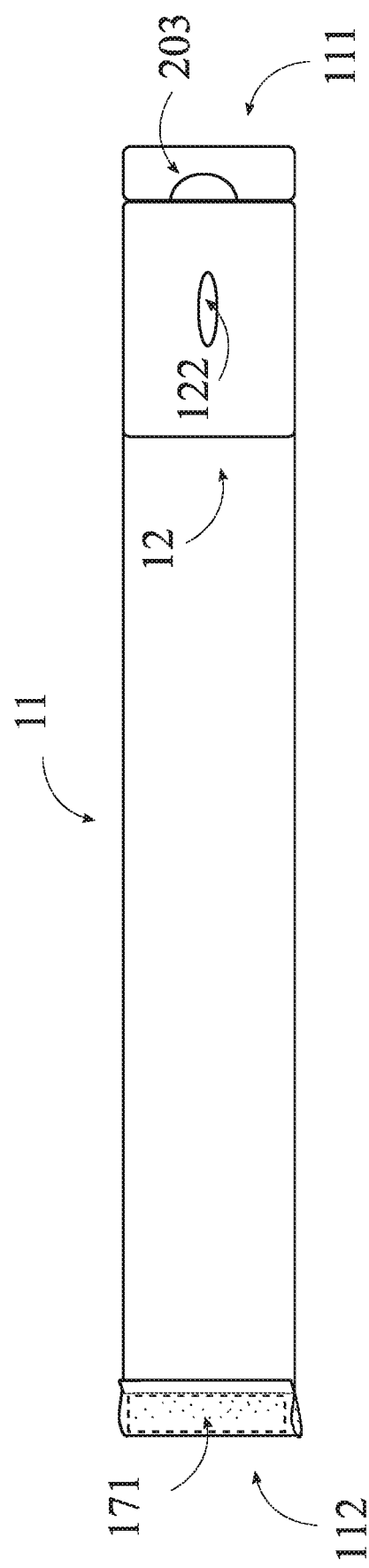
FIG. 2 is a rear view of the present invention.

The assembly centers about a primary dressing that may be used for moderate to substantial wounds where an elastic band is housed within or on top of the primary dressing. A tightening rod is secured to the elastic band to impart the functionality of a conventional tourniquet to the primary dressing in association with a tightening buckle that fastens to the primary dressing.

Through a primary mounting sheet and a secondary mounting sheet, a primary adhesive section of the primary dressing is exposed, adhering to a wounded individual and aiding in stemming the flow of outside air from the individuals wound by facilitating an airtight seal about the wound. Further, the present invention permits the assembly to firstly pressure and staunch a wound. Through removing the primary mounting sheet from the secondary mounting sheet, the secondary adhesive section of a secondary dressing is exposed, permitting the second dressing to address a lesser wound either isolated from or simultaneous with the primary dressing. Further, the secondary dressing comprises an absorbent pad pocket and a slit that houses a tertiary dressing. The tertiary dressing may be extracted from the absorbent pad pocket by pulling the tertiary dressing through the slit. This permits the application of the tertiary dressing that may be used in isolation from the primary and secondary dressing, or in combination therewith to address a variety of wounds to at least one recipient. Thus, by localizing the secondary dressing to the primary dressing modularly, and the tertiary dressing to the secondary dressing, the assembly affords a larger spectrum of injuries to be addressed by a single combinate tool. The elastic band housed on the primary dressing and a retaining clip on the distal end thereof permits the primary dressing to further operate as a tourniquet which can be tightened by twisting the tightening rod. By localizing all of the constituent elements of a trauma kit to a single apparatus where the constituent components thereof may be modularly removed, the apparatus ensures that the misplacement or negligence in resupply of a single component is substantially mitigated by combining all smaller elements to the larger primary dressing, thereby affording the user to more immediately address a wound of indeterminate intensity with a single comprehensive tool and further facilitate convenient transportation of the apparatus.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

In reference to FIGS. 1-7, the present invention is a medical bandaging and tourniquet system 1 comprising a primary dressing 11, a secondary dressing 12, a band 13, a tightening buckle 14, and a tightening rod 16. The primary dressing 11 extends between a first primary dressing end 111 and a second primary dressing end 112. In reference to FIGS. 1-2, and 4-5, the primary dressing 11 serves as the major wrapping bandage of the medical bandaging and tourniquet system 1, serving as the main bandage wrap that supports the mounting of the tourniquet wrapping components of the medical bandaging and tourniquet system 1. Additionally, the primary dressing 11 supports the mounting of the secondary dressing 12 such that the secondary dressing 12 is removably attached from the primary dressing 11. In the preferred embodiment of the present invention, the primary dressing 11 is made out of a textile, porous and/or absorbent material such as cloth. Although other materials may be employed, such as, but not limited to cotton, elastics, textiles, or any other suitable material. In the preferred embodiment of the present invention, the primary dressing 11 preferably is a near rectilinear planar or flattened cubic body that possesses a longitudinal dimension but may take the form of any other corresponding shape. In the preferred embodiment of the present invention, the primary dressing 11 possesses a relatively planar top and bottom surface that is malleable and deformable but may take the form of any other corresponding shape.

In reference to FIG. 1, the first primary dressing end 111 is the primary dressing portion that supports the tourniquet and bandaging components of the medical bandaging and tourniquet system 1. In the preferred embodiment of the present invention, the first primary dressing end 111 serves as the wound installment portion of the primary dressing 11, allowing the user to dress a wound along the first primary dressing 11 portion. In the preferred embodiment of the present invention, the second primary dressing end 112 is opposite to the first primary dressing end 111 along the primary dressing 11, serving as the wrapping end of the primary dressing 11. More specifically, the second primary dressing end 112 allows the user to pull and wrap the second primary dressing end 112 along the primary dressing 11.

In reference to FIGS. 2, and 4-6, the secondary dressing 12 is removably attached adjacent to the first primary dressing end 111. The secondary dressing 12 comprises an absorbent pad pocket 121, a slit 122, and a tertiary dressing 123. In the preferred embodiment of the present invention, the secondary dressing 12 may take the form of an independent bandage that treats minor wounds in conjunction with the primary dressing 11. In the preferred embodiment of the present invention, the secondary dressing 12 is made out of a textile, porous and/or absorbent material such as cloth. Other materials may also be employed such as but not limited to cotton, elastics, textiles, or any other suitable material. In the preferred embodiment of the present invention, the secondary dressing 12 is a near rectilinear planar or flattened cubic body that possesses a longitudinal dimension but may take the form of any size. In the preferred embodiment of the present invention, the secondary dressing 12 possesses a relatively planar top and bottom surface that is malleable and deformable but may take the form of any other corresponding shape. In reference to FIG. 6, the absorbent pad pocket 121 is positioned within the secondary dressing 12. The absorbent pad pocket 121 may take the form of an internal cavity that facilitates the storage of the tertiary dressing 123 within the secondary dressing 12. In reference to FIGS. 2, 4, and 6, the slit 122 traverses through the secondary dressing 12 into the absorbent pad pocket 121. In the preferred embodiment of the present invention, the slit 122 may take the form of an access opening, allowing the user to pull and dispense the tertiary dressing 123 from within the secondary dressing 12. In reference to FIG. 6, the tertiary dressing 123 is positioned within the absorbent pad pocket 121. In the preferred embodiment of the present invention, the tertiary dressing 123 may take the form of gauze bandage dressing that allows the user to dress a wound in conjunction with the secondary dressing 12 and the primary dressing 11. In the preferred embodiment of the present invention, the tertiary dressing 123 may take the form of any suitable bandaging material for dressing wounds such as but not limited to medical grade silk, linen, cotton, or any other suitable bandaging material.

Figure 3:
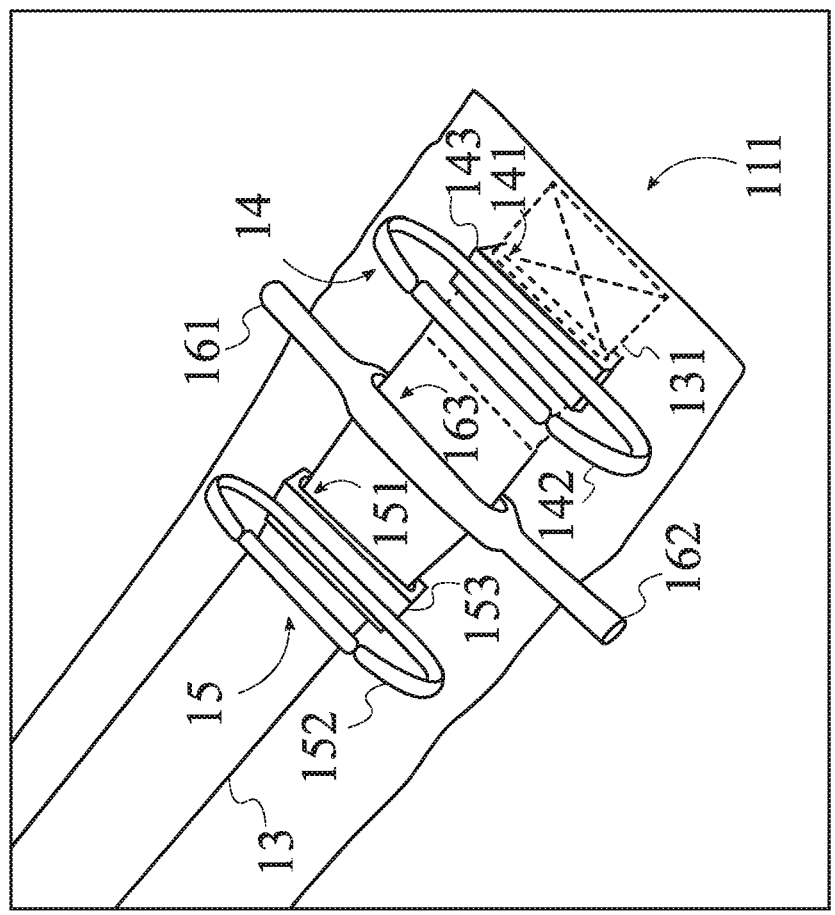
FIG. 3 is a detailed diagram view of the present invention that shows a first primary dressing end.

In reference to FIGS. 1 and 3, the band 13 extends between a first band end 131 and a second band end 132. The band 13 is positioned adjacent to the primary dressing 11 opposite to the secondary dressing 12. In the preferred embodiment of the present invention, the band 13 may take the form of an elastic strip that serves as the compressive support member of the primary dressing 11 when the primary dressing 11 is stretched and wrapped around the wound area. In the preferred embodiment of the present invention, the band 13 may take the form of any elastic fabric made out a suitable material such as but not limited to rubber, silicone, metal springs, or any other suitable elastic tensile supportive material. In reference to FIGS. 1, and 3, the first band end 131 is connected to the primary dressing 11 adjacent to the first primary dressing end 111. The first band end 131 serves as the portion of the band 13 that is attached to the first primary dressing end 111. In the preferred embodiment of the present invention, the first band end 131 is sewn on to the first primary dressing end 111 but can be fixed through any other means such as, but not limited to adhesive, molding, or any other fastening means. In reference to FIG. 1, the second band end 132 is connected to the primary dressing 11 between the first primary dressing end 111 and the second primary dressing end 112. In the preferred embodiment of the present invention, the second band end 132 is sewn on to the first primary dressing end 111 but can be affixed through and other means, similar to the first band end 131.

In reference to FIGS. 1 and 3, the tightening buckle 14 comprises a buckle anchor 143, a buckle aperture 141 and a buckle frame 142. The tightening buckle 14 is connected to the primary dressing 11 adjacent to the first primary dressing end 111. The tightening buckle 14 serves as the strapping member that allows the user to pass and pull the second primary dressing end 112 through the tightening buckle 14 to firmly strap and secure the primary dressing 11 along the wound. In the preferred embodiment of the present invention, the buckle aperture 141 traverses through the buckle anchor 143. The buckle anchor mounts and secures the tightening buckle 14 to the band 13. In the preferred embodiment of the present invention, the band 13 is positioned through the buckle aperture 141. The buckle aperture 141 serves as the attachment opening of the tightening buckle 14 in securing the band 13 to the tightening buckle 14. In the preferred embodiment of the present invention, the buckle aperture 141 can further be fixed with an adhesive along the primary dressing 11 but can be attached through any other fastening means. The buckle frame 142 is positioned adjacent to the buckle anchor 143. In the preferred embodiment of the present invention, the buckle frame 142 may take the form of a belt buckle strap frame that allows the user to pass and pull the second primary dressing end 112 through the buckle frame 142 to firmly strap and secure the primary dressing 11 along the wound.

In reference to FIGS. 1, and 3, the retaining clip 15 comprises a retaining clip anchor 153, a retaining clip aperture 151 and a retaining clip catch 152. The retaining clip 15 is spaced apart from the tightening buckle 14 towards the second primary band 13 end. In the preferred embodiment of the present invention, the retaining clip 15 is connected to the primary dressing 11. The retaining clip 15 serves as an anchor clip for the tightening rod 16 that allows the user to removably attach the tightening rod 16 to the retaining clip 15, tying and locking the torque from the turned tightening rod 16. In the preferred embodiment of the present invention, the retaining clip aperture 151 traverses through the retaining clip anchor 153. The retaining clip anchor 153 mounts and secures the retaining clip 15 to the band 13. In the preferred embodiment of the present invention, the band 13 is positioned through the retaining clip aperture 151. The retaining clip aperture 151 serves as the attachment portion of the tightening buckle 14 in securing the band 13 to the retaining clip 15. In the preferred embodiment of the present invention, the retaining clip aperture 151 can further be fixed with an adhesive along the primary dressing 11 but can be attached through any other fastening means. The retaining clip catch 152 is positioned adjacent to the retaining clip anchor 153. In the preferred embodiment of the present invention, the retaining clip catch 152 serves as the portion of the retaining clip 15 that engages the turned tightening rod 16, tying and locking the torque from the turned tightening rod 16.

In reference to FIGS. 1, and 3, the tightening rod 16 comprises a first tightening rod end 161, a second tightening rod end 162, and a band aperture 163. The tightening rod 16 is connected to the band 13 between the retaining clip 15 and the tightening buckle 14. In the preferred embodiment of the present invention, the tightening rod 16 may take the form of a tourniquet style compressive crank that allows the user to apply further compression along the wrapped primary dressing 11 and band. The tightening rod 16 extends between the first tightening rod end 161 and the second tightening rod end 162. The first tightening rod end 161 and the second tightening rod end 162 serves as turn crank handles that allows the user to wind the tightening rod 16 along the band. The compressing band 13 acts upon the primary dressing 11, facilitating tourniquet-style compression treatment along the wound. The band aperture 163 is positioned between the first tightening rod end 161 and the second tightening rod end 162. The band 13 is also positioned through the band aperture 163. The band aperture 163 serves as the attachment portion of the tightening rod 16 in securing the band 13 to the tightening rod 16.

In reference to FIGS. 1-6, the medical bandaging and tourniquet further comprises a fastening clip 17. In reference to FIGS. 1-2, the fastening clip 17 comprises a plurality of fasteners 171. The fastening clip 17 is positioned adjacent to the second primary dressing end 112. In the preferred embodiment of the present invention, the fastening clip 17 may take the form of a hook style fastener clip that facilitates the removable attachment of the fastening clip 17 to the primary dressing 11 when the primary dressing 11 is wrapped along a wound. In the preferred embodiment of the present invention, the fastening clip 17 may take the form of any suitable fastener such as but not limited to clamp, adhesive, pin, or any other suitable type of fastener clip. In the preferred embodiment of the present invention, the plurality of fasteners 171 is positioned along the fastening clip 17, where the second primary dressing end 112 is removably attached to the primary dressing 11 through the plurality of fasteners 171. In the preferred embodiment of the present invention, the plurality of fasteners 171 may take the form of fastening hooks that engages the fabric surface of the primary dressing 11, allowing the fastening clip 17 to removably attach on to the primary dressing 11 to secure the second primary dressing end 112 on to wrapped primary dressing 11.

In reference to FIG. 1, the medical bandaging and tourniquet further comprises a fastening clip 17, an indicium panel 18. In reference to FIG. 1, the indicium panel 18 is positioned adjacent to the primary dressing 11. In the preferred embodiment of the present invention, the indicium panel 18 is positioned near the second primary dressing end 112. The indicium panel 18 serves as a legible surface that allows the user to write and mark an indicium indicating useful first-aid information to first responders, or any other medical correspondent.

In reference to FIGS. 1-6, the medical bandaging and tourniquet further comprises a primary mounting sheet 19 and a secondary mounting sheet 20. In reference to FIGS. 4-5, the primary mounting sheet 19 is connected adjacent to the first primary dressing end 111. In the preferred embodiment of the present invention, the primary mounting sheet 19 may take the form of a mounting layer that facilitates the removable attachment of the primary dressing 11 to the secondary dressing 12. Furthermore, the primary mounting sheet 19 serves as the adhesive portion of the primary dressing 11 that allows the user to adhere the first primary dressing end 111 on to a wound. In the preferred embodiment of the present invention, the primary mounting sheet 19 can be made out of any suitable layer that can be attached on to the primary dressing 11 such as, but not limited to plastic film, plastic mesh, fibrous mesh, or any other suitable attaching layer.

Figure 4:
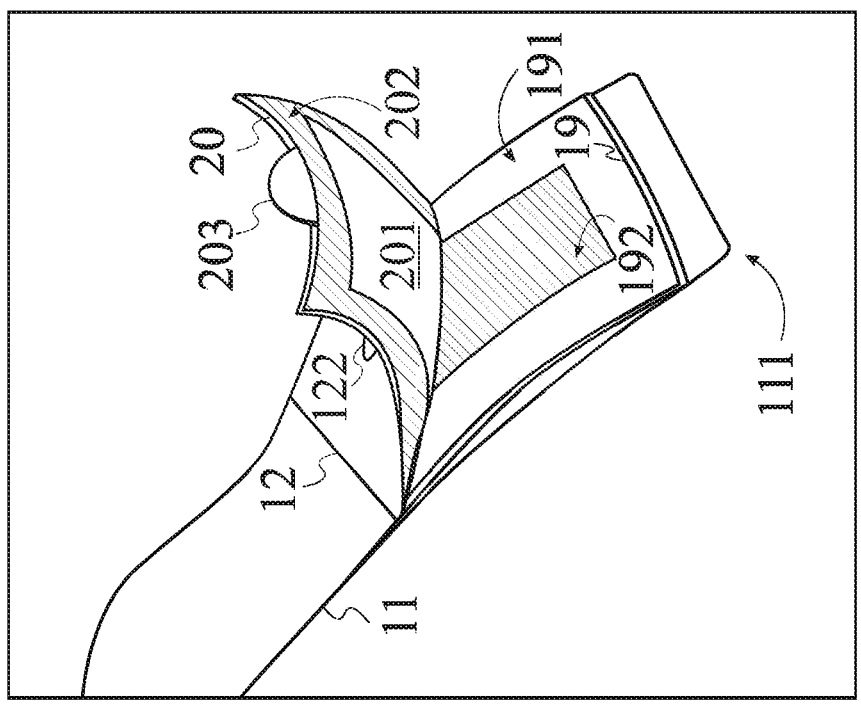
FIG. 4 is a detailed diagram view of the present invention that shows a secondary dressing being peeled off from the primary dressing.

In reference to FIG. 4, the secondary mounting sheet 20 is connected adjacent to the secondary dressing 12; more particularly, the secondary mounting sheet 20 is layered adjacent to the secondary dressing 12. In the preferred embodiment of the present invention, the secondary mounting sheet 20 is removably attached to the primary mounting sheet 19. The secondary mounting sheet 20 may take the form of the mounting layer that facilitates the removable attachment of the primary dressing 11 to the secondary dressing 12. Furthermore, the secondary mounting sheet 20 serves as the adhesive portion of the secondary dressing 12 that allows the user to adhere the second primary dressing end 112 on to a wound.

Figure 5:
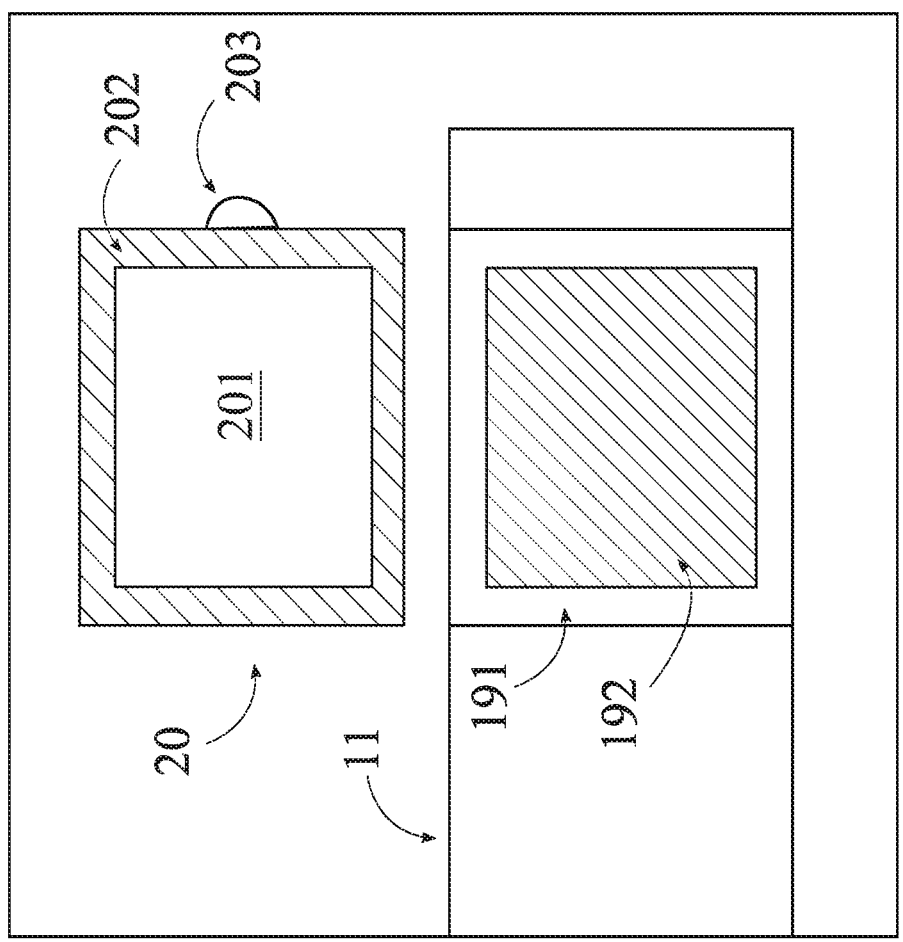
FIG. 5 is a detailed diagram view of the present invention that shows the secondary dressing separated from the primary dressing.
Figure 6:
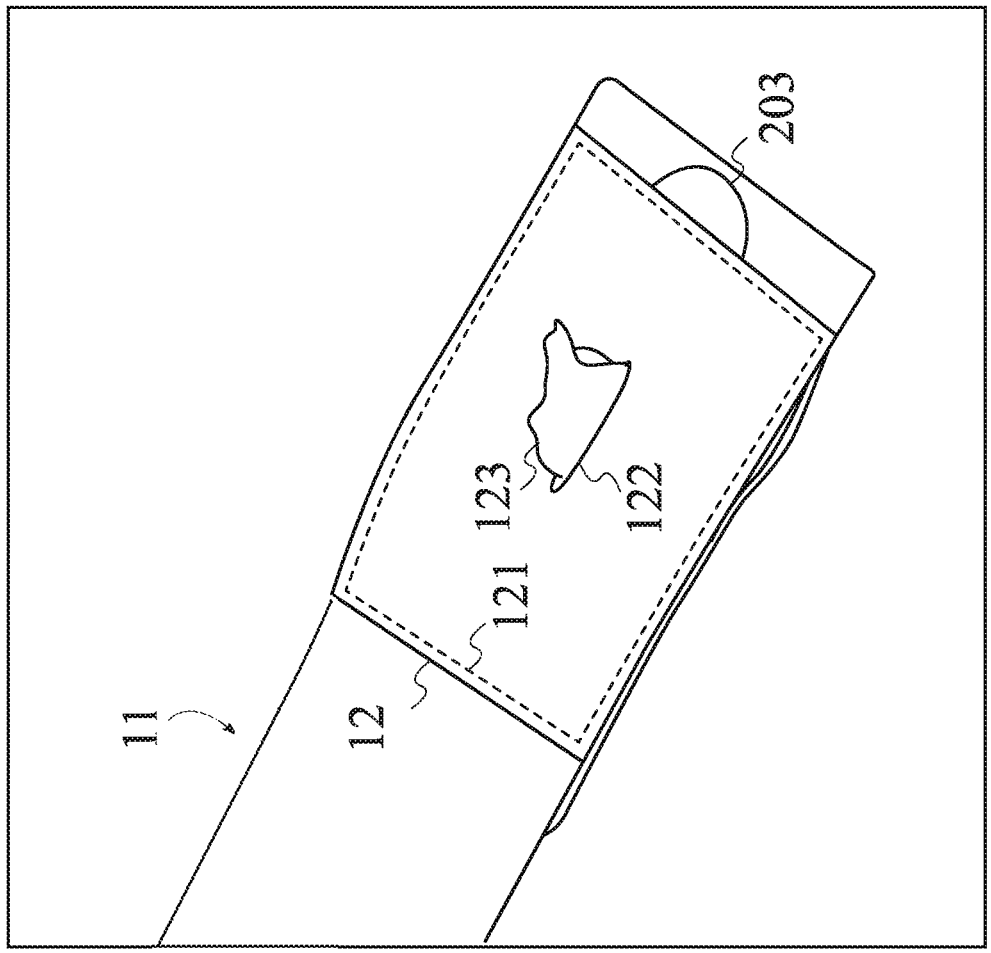
FIG. 6 is a detailed diagram view of the secondary dressing.

In reference to FIGS. 4-5, the primary mounting sheet 19 comprises a primary divider section 191 and a primary adhesive section 192. The secondary mounting sheet 20 comprises a secondary divider section 201, a secondary adhesive section 202, and a pull tab 203. The primary divider section 191 is perimetrically positioned on the primary mounting sheet 19, and the primary adhesive section 192 is positioned within the primary divider section 191. Similarly, the secondary adhesive section 202 is perimetrically positioned on the secondary mounting sheet 20, while the secondary divider section 201 is positioned within the secondary adhesive section 202. The primary divider section 191 is removably attached to the secondary adhesive section 202, and the secondary divider section 201 is removably attached to the primary adhesive section 192. In the preferred embodiment of the present invention, the primary divider section 191 and the secondary divider section 201 serve as the non-stick surface portions of the primary mounting sheet 19 and the secondary mounting sheet 20 that allow the primary adhesive section 192 and the secondary adhesive section 202 to easily peel off from the primary mounting sheet 19 and the secondary mounting sheet 20, respectively. The perimetrically positioned secondary adhesive section 202 along the secondary mounting sheet 20 serves as a seal for the secondary dressing 12, allowing the user to close off a minor wound with the secondary dressing 12. The primary adhesive section 192, along the primary mounting sheet 19 serves as an attachment means in installing the primary dressing 11 along a wound. In the preferred embodiment of the present invention, the primary adhesive section 192 and the secondary adhesive section 202 may take the form of adhesive hyrdogel in some embodiments, but in various embodiments may take various suitable forms, such as, but not limited to any other suitable medical grade adhesive. In the preferred embodiment of the present invention, the pull tab 203 is terminally connected adjacent to the secondary mounting sheet 20. The pull tab 203 allows the user to grasp and peel the secondary dressing 12 from the primary dressing 11.

Figure 7:
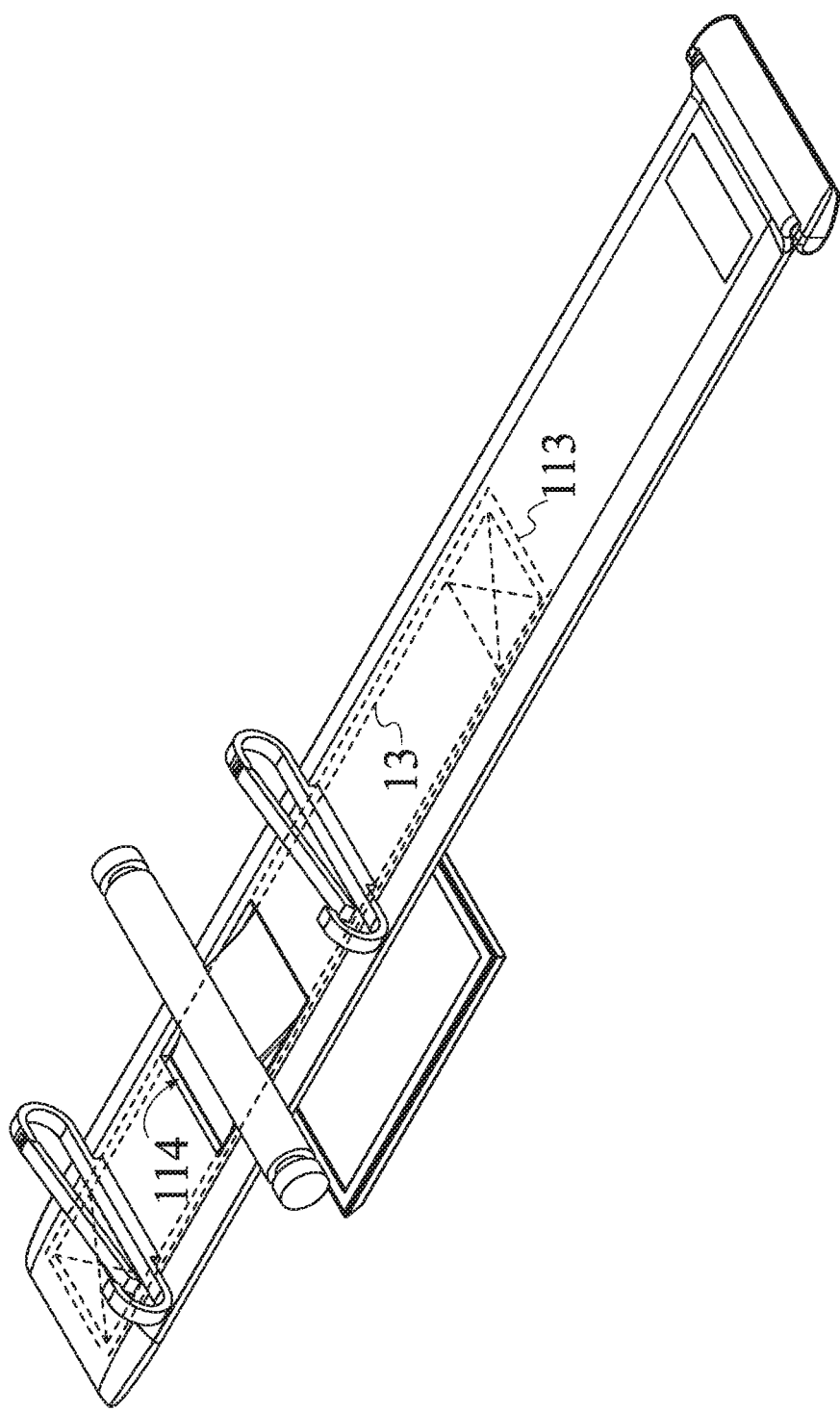
FIG. 7 is a perspective view of the present invention, in accordance to another embodiment.

In another embodiment of the present invention, the primary dressing 11 further comprises a band cavity 113 and a primary dressing aperture 114, as shown in FIG. 7. In this embodiment, the band cavity 113 is positioned within the primary dressing 11. The band cavity 113 houses the band 13 within the primary dressing 11. The primary dressing aperture 114 is positioned between the tightening buckle 14 and the retaining clip 15. Additionally, the primary dressing aperture 114 traverses through the primary dressing 11 into the band cavity 113. The primary dressing aperture 114 serves as an access opening, allowing the band 13 to emerge out of the primary dressing 11.

Although the invention has been explained in relation to its preferred embodiment, it is to be understood that many other possible modifications and variations can be made without departing from the spirit and scope of the invention.

What is claimed is:

1. A medical bandaging and tourniquet system comprising:
    a primary dressing;
    a secondary dressing;
    a band;
    a tightening buckle;
    a retaining clip;
    a tightening rod;
    a primary mounting sheet;
    a secondary mounting sheet;
    the primary dressing extending between a first primary dressing end and a second primary dressing end;
    the band extending between a first band end and a second band end;
    the secondary dressing being removably attached adjacent to the first primary dressing end;
    the band being positioned adjacent to the primary dressing opposite to the secondary dressing;
    the first band end being connected to the primary dressing adjacent to the first primary dressing end;
    the second band end being connected to the primary dressing between the first primary dressing end and the second primary dressing end;
    the tightening buckle being connected to the primary dressing adjacent to the first primary dressing end;
    the retaining clip being connected to the primary dressing;
    the retaining clip being spaced apart from the tightening buckle towards the second primary band end;
    the tightening rod being connected to the band between the retaining clip and the tightening buckle;
    the primary mounting sheet being connected adjacent to the first primary dressing end;
    the secondary mounting sheet being connected adjacent to the secondary dressing;
    the secondary mounting sheet being removably attached to the primary mounting sheet;
    the primary mounting sheet comprising a primary divider section and a primary adhesive section;
    the secondary mounting sheet comprising a secondary divider section, a secondary adhesive section, and a pull tab;
    the primary divider section being perimetrically positioned on the primary mounting sheet;
    the primary adhesive section being positioned within the primary divider section;
    the secondary adhesive section being perimetrically positioned on the secondary mounting sheet;
    the secondary divider section being positioned within the secondary adhesive section;
    the primary divider section being removably attached to the secondary adhesive section;
    the secondary divider section being removably attached to the primary adhesive section; and
    the pull tab being terminally connected adjacent to the secondary mounting sheet.

2. The medical bandaging and tourniquet system as claimed in claim 1 comprising:
    a fastening clip;
    the fastening clip comprising a plurality of fasteners;
    the fastening clip being positioned adjacent to the second primary dressing end; and
    the plurality of fasteners being positioned along the fastening clip, wherein the second primary dressing end is removably attached to the primary dressing through the plurality of fasteners.

3. The medical bandaging and tourniquet system as claimed in claim 1 comprising:
    the secondary dressing comprising an absorbent pad pocket, a slit, and a tertiary dressing;
    the absorbent pad pocket being positioned within the secondary dressing;
    the slit traversing through the secondary dressing into the absorbent pad pocket; and
    the tertiary dressing being positioned within the absorbent pad pocket.

4. The medical bandaging and tourniquet system as claimed in claim 1 comprising:
    an indicium panel; and
    the indicium panel being positioned adjacent to the primary dressing.

5. The medical bandaging and tourniquet system as claimed in claim 1 comprising:
    the primary dressing further comprising a band cavity, and a primary dressing aperture;
    the band cavity being positioned within the primary dressing;
    the primary dressing aperture being positioned between the tightening buckle and the retaining clip; and
    the primary dressing aperture traversing through the primary dressing into the band cavity.

6. The medical bandaging and tourniquet system as claimed in claim 1 comprising:
    the tightening rod comprising a first tightening rod end, a second tightening rod end, and a band aperture;
    the tightening rod extending between the first tightening rod end and the second tightening rod end;
    the band aperture being positioned between the first tightening rod end and the second tightening rod end; and
    the band being positioned through the band aperture.

7. The medical bandaging and tourniquet system as claimed in claim 1 comprising:
    the tightening buckle comprising a buckle anchor, a buckle aperture and a buckle frame;
    the buckle aperture traversing through the buckle anchor;
    the band being positioned though the buckle aperture; and
    the buckle frame being positioned adjacent to the buckle anchor.

8. The medical bandaging and tourniquet system as claimed in claim 1 comprising:
    the retaining clip comprising a retaining clip anchor, a retaining clip aperture and a retaining clip catch;
    the retaining clip aperture traversing through the retaining clip anchor;
    the band being positioned through the retaining clip aperture; and
    the retaining clip catch being positioned adjacent to the retaining clip anchor.

* * * * *